(12) United States Patent
Hayashi et al.

(10) Patent No.: US 8,859,241 B2
(45) Date of Patent: Oct. 14, 2014

(54) PROCESS FOR PRODUCTION OF L-AMINO ACID

(75) Inventors: Mikiro Hayashi, Ibaraki (JP); Kazuhiko Tabata, Los Angeles, CA (US)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 172 days.

(21) Appl. No.: 13/520,954

(22) PCT Filed: Jan. 7, 2011

(86) PCT No.: PCT/JP2011/050208
§ 371 (c)(1),
(2), (4) Date: Sep. 6, 2012

(87) PCT Pub. No.: WO2011/083860
PCT Pub. Date: Jul. 14, 2011

(65) Prior Publication Data
US 2012/0329106 A1    Dec. 27, 2012

(30) Foreign Application Priority Data
Jan. 8, 2010    (JP) .................. 2010-002704

(51) Int. Cl.
*C12P 13/04* (2006.01)
*C12N 9/00* (2006.01)
*C12N 1/20* (2006.01)
*C12N 15/00* (2006.01)
*C07H 21/02* (2006.01)
*C12P 13/14* (2006.01)
*C12R 1/19* (2006.01)

(52) U.S. Cl.
CPC ................. *C12P 13/04* (2013.01); *C12P 13/14* (2013.01); *C12Y 301/02012* (2013.01); *C12R 1/19* (2013.01)
USPC ..... 435/106; 435/183; 435/252.3; 435/320.1; 536/23.2

(58) Field of Classification Search
None
See application file for complete search history.

(56) References Cited

FOREIGN PATENT DOCUMENTS

| JP | 55-148094 A | 11/1980 |
|---|---|---|
| JP | 01-312996 A | 12/1989 |
| JP | 03-232497 A | 10/1991 |
| JP | 2002-300887 A | 10/2002 |
| JP | 2003-164297 A | 6/2003 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Gonzales et al., *The Journal of Biological Chemistry*, 281(20): 14514-14522 (2006).
Jakoby et al., *FEMS Microbiology Letters*, 173:: 303-310 (1999).
Nolden et al., *FEMS Microbiology Letters, 201*: 91-98 (2001).
Japanese Patent Office, International Search Report in International Patent Application No. PCT/JP2011/050208 (Feb. 8, 2011).

* cited by examiner

*Primary Examiner* — Christian Fronda
(74) *Attorney, Agent, or Firm* — Leydig, Voit & Mayer, Ltd.

(57) ABSTRACT

Provided is a novel process for producing an L-amino acid using a microorganism belonging to the genus *Escherichia*. According to the present invention, a process for producing an L-amino acid comprising; culturing a microorganism in which an activity of the protein of any of the following [1]-[3] is increased compared with that of the parent strain in a medium, producing and accumulating the L-amino acid in the medium, and recovering the L-amino acid from the medium:

[1] a protein comprising the amino acid sequence shown in SEQ ID NO: 2

[2] a protein consisting of an amino acid sequence in which one or more amino acids are deleted, substituted or added in the amino acid sequence shown in SEQ ID NO: 2, and having YeiG activity

[3] a protein consisting of an amino acid sequence having 80% or more homology to the amino acid sequence shown in SEQ ID NO: 2, and having YeiG activity.

13 Claims, No Drawings

SEQUENCE LISTING

```
<160> NUMBER OF SEQ ID NOS: 26

<210> SEQ ID NO 1
<211> LENGTH: 837
<212> TYPE: DNA
<213> ORGANISM: Escherichia coli
<220> FEATURE:
<221> NAME/KEY: CDS
<222> LOCATION: (1)..(837)

<400> SEQUENCE: 1 atg gaa atg ctc gaa gag cac cgc tgt ttt gaa ggc tgg cag caa cgc       48
Met Glu Met Leu Glu Glu His Arg Cys Phe Glu Gly Trp Gln Gln Arg
1               5                   10                  15 tgg cga cac gac tcc agt acc tta aac tgc ccg atg acg ttc agt atc       96
Trp Arg His Asp Ser Ser Thr Leu Asn Cys Pro Met Thr Phe Ser Ile
                20                  25                  30 ttt ctc cct cca cct cgt gat cac act ccg cca cca gtg ctg tac tgg      144
Phe Leu Pro Pro Pro Arg Asp His Thr Pro Pro Pro Val Leu Tyr Trp
            35                  40                  45 ctt tcc gga tta acc tgc aat gac gag aac ttc acc acc aag gcg ggt      192
Leu Ser Gly Leu Thr Cys Asn Asp Glu Asn Phe Thr Thr Lys Ala Gly
        50                  55                  60
```

```
gcc cag cgg gta gcg gcg gaa ctg ggg att gta ctg gtg atg cca gac       240
Ala Gln Arg Val Ala Ala Glu Leu Gly Ile Val Leu Val Met Pro Asp
 65              70                  75                  80 acc agc ccg cgc ggc gaa aag gtt gcc aac gat gat ggc tac gat tta       288
Thr Ser Pro Arg Gly Glu Lys Val Ala Asn Asp Asp Gly Tyr Asp Leu
             85                  90                  95 ggc cag ggc gca ggc ttt tat ctt aat gcc acg caa ccg ccg tgg gcg       336
Gly Gln Gly Ala Gly Phe Tyr Leu Asn Ala Thr Gln Pro Pro Trp Ala
            100                 105                 110 acg cat tac cgg atg tat gat tat ctg cgc gat gaa tta ccg gcg ctg       384
Thr His Tyr Arg Met Tyr Asp Tyr Leu Arg Asp Glu Leu Pro Ala Leu
        115                 120                 125 gtt cag tcg caa ttt aat gtc agc gac cgc tgc gcc att agc ggt cac       432
Val Gln Ser Gln Phe Asn Val Ser Asp Arg Cys Ala Ile Ser Gly His
        130                 135                 140 tca atg ggt ggt cac ggt gcg ctg att atg gcg ctg aaa aat ccg ggt       480
Ser Met Gly Gly His Gly Ala Leu Ile Met Ala Leu Lys Asn Pro Gly
145                 150                 155                 160 aaa tac acc agc gtt tcg gcc ttt gcg cca att gtg aat ccg tgc agc       528
Lys Tyr Thr Ser Val Ser Ala Phe Ala Pro Ile Val Asn Pro Cys Ser
                165                 170                 175 gtc ccg tgg gga atc aaa gcg ttt agc agc tat tta ggt gag gac aaa       576
Val Pro Trp Gly Ile Lys Ala Phe Ser Ser Tyr Leu Gly Glu Asp Lys
            180                 185                 190 aat gca tgg ctg gaa tgg gac agt tgc gca ctg atg tat gcc agt aac       624
Asn Ala Trp Leu Glu Trp Asp Ser Cys Ala Leu Met Tyr Ala Ser Asn
        195                 200                 205 gcg cag gat gcg atc ccg acg ctt atc gat cag ggc gat aat gat cag       672
Ala Gln Asp Ala Ile Pro Thr Leu Ile Asp Gln Gly Asp Asn Asp Gln
        210                 215                 220 ttt ctt gcc gac cag ttg caa cct gcg gta ctg gca gaa gcc gcg cgc       720
Phe Leu Ala Asp Gln Leu Gln Pro Ala Val Leu Ala Glu Ala Ala Arg
225                 230                 235                 240 cag aaa gcg tgg ccg atg acg ctg cgt att cag ccg gga tat gat cac       768
Gln Lys Ala Trp Pro Met Thr Leu Arg Ile Gln Pro Gly Tyr Asp His
                245                 250                 255 agt tac tac ttc atc gcc tct ttt ata gag gat cac ctg cgc ttc cat       816
Ser Tyr Tyr Phe Ile Ala Ser Phe Ile Glu Asp His Leu Arg Phe His
            260                 265                 270 gcg cag tat tta ctg aag tga                                           837
Ala Gln Tyr Leu Leu Lys
        275

<210> SEQ ID NO 2
<211> LENGTH: 278
<212> TYPE: PRT
<213> ORGANISM: Escherichia coli

<400> SEQUENCE: 2

Met Glu Met Leu Glu Glu His Arg Cys Phe Glu Gly Trp Gln Gln Arg
1               5                   10                  15

Trp Arg His Asp Ser Ser Thr Leu Asn Cys Pro Met Thr Phe Ser Ile
                20                  25                  30

Phe Leu Pro Pro Pro Arg Asp His Thr Pro Pro Val Leu Tyr Trp
            35                  40                  45

Leu Ser Gly Leu Thr Cys Asn Asp Glu Asn Phe Thr Thr Lys Ala Gly
        50                  55                  60

Ala Gln Arg Val Ala Ala Glu Leu Gly Ile Val Leu Val Met Pro Asp
65                  70                  75                  80
```

```
Thr Ser Pro Arg Gly Glu Lys Val Ala Asn Asp Asp Gly Tyr Asp Leu
            85                  90                  95

Gly Gln Gly Ala Gly Phe Tyr Leu Asn Ala Thr Gln Pro Pro Trp Ala
        100                 105                 110

Thr His Tyr Arg Met Tyr Asp Tyr Leu Arg Asp Glu Leu Pro Ala Leu
        115                 120                 125

Val Gln Ser Gln Phe Asn Val Ser Asp Arg Cys Ala Ile Ser Gly His
    130                 135                 140

Ser Met Gly Gly His Gly Ala Leu Ile Met Ala Leu Lys Asn Pro Gly
145                 150                 155                 160

Lys Tyr Thr Ser Val Ser Ala Phe Ala Pro Ile Val Asn Pro Cys Ser
                165                 170                 175

Val Pro Trp Gly Ile Lys Ala Phe Ser Ser Tyr Leu Gly Glu Asp Lys
            180                 185                 190

Asn Ala Trp Leu Glu Trp Asp Ser Cys Ala Leu Met Tyr Ala Ser Asn
        195                 200                 205

Ala Gln Asp Ala Ile Pro Thr Leu Ile Asp Gly Asp Asn Asp Gln
    210                 215                 220

Phe Leu Ala Asp Gln Leu Gln Pro Ala Val Leu Ala Glu Ala Ala Arg
225                 230                 235                 240

Gln Lys Ala Trp Pro Met Thr Leu Arg Ile Gln Pro Gly Tyr Asp His
                245                 250                 255

Ser Tyr Tyr Phe Ile Ala Ser Phe Ile Glu Asp His Leu Arg Phe His
            260                 265                 270

Ala Gln Tyr Leu Leu Lys
        275

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA

<400> SEQUENCE: 3
tttaagctta cacaacaagg agccacgca                                    29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA

<400> SEQUENCE: 4
tttgagctcc ggactttcac ttcagtaaa                                    29

<210> SEQ ID NO 5
<211> LENGTH: 29
<212> TYPE: DNA
<213> ORGANISM: Artificial Sequence
<220> FEATURE:
<223> OTHER INFORMATION: Synthetic DNA

<400> SEQUENCE: 5
tttgtcgaca gaataaataa atcctggtg                                    29

<210> SEQ ID NO 6
<211> LENGTH: 20
<212> TYPE: DNA
```

```
<213> ORGANISM: Artificial Sequence
<220> FEATURE:
<223> OTHER INFORMATION: Synthetic DNA

<400> SEQUENCE: 6
cacttattca ggcgtagcac                                                  20

<210> SEQ ID NO 7
<211> LENGTH: 29
<212> TYPE: DNA
<213> ORGANISM: Artificial Sequence
<220> FEATURE:
<223> OTHER INFORMATION: Synthetic DNA

<400> SEQUENCE: 7
tttgtcgact ttaggcccgt agtctgcaa                                        29

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
tatcggcatt ttcttttgcg                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
tcgtatttca gacctgttgc                                                  20

<210> SEQ ID NO 10
<211> LENGTH: 40
<212> TYPE: DNA
<213> ORGANISM: Artificial Sequence
<220> FEATURE:
<223> OTHER INFORMATION: Synthetic DNA

<400> SEQUENCE: 10
cgcaaaagaa aatgccgata gattctctgc cattcaattt                            40

<210> SEQ ID NO 11
<211> LENGTH: 40
<212> TYPE: DNA
<213> ORGANISM: Artificial Sequence
<220> FEATURE:
<223> OTHER INFORMATION: Synthetic DNA

<400> SEQUENCE: 11
tttgcatcac ccggttttat gattctctgc cattcaattt                            40

<210> SEQ ID NO 12
<211> LENGTH: 40
<212> TYPE: DNA
<213> ORGANISM: Artificial Sequence
<220> FEATURE:
<223> OTHER INFORMATION: Synthetic DNA

<400> SEQUENCE: 12
gtgctacgcc tgaataagtg ataaaaccgg gtgatgcaaa                            40
```

<210> SEQ ID NO 13
<211> LENGTH: 40
<212> TYPE: DNA
<213> ORGANISM: Artificial Sequence
<220> FEATURE:
<223> OTHER INFORMATION: Synthetic DNA

<400> SEQUENCE: 13
aaattgaatg gcagagaatc ataaaaccgg gtgatgcaaa                           40

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
ctgcgaagcc gacacccttg                                                20

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA

<400> SEQUENCE: 15
atctcgcctc ccgcgtgcag                                                20

<210> SEQ ID NO 16
<211> LENGTH: 40
<212> TYPE: DNA
<213> ORGANISM: Artificial Sequence
<220> FEATURE:
<223> OTHER INFORMATION: Synthetic DNA

<400> SEQUENCE: 16
cgcaaaagaa aatgccgata aagcgatttt atccttgcct                          40

<210> SEQ ID NO 17
<211> LENGTH: 40
<212> TYPE: DNA
<213> ORGANISM: Artificial Sequence
<220> FEATURE:
<223> OTHER INFORMATION: Synthetic DNA

<400> SEQUENCE: 17
gcgcgcgata ataccatact aagcgatttt atccttgcct                          40

<210> SEQ ID NO 18
<211> LENGTH: 40
<212> TYPE: DNA
<213> ORGANISM: Artificial Sequence
<220> FEATURE:
<223> OTHER INFORMATION: Synthetic DNA

<400> SEQUENCE: 18
gtgctacgcc tgaataagtg agtatggtat tatcgcgcgc                          40

<210> SEQ ID NO 19
<211> LENGTH: 40
<212> TYPE: DNA
<213> ORGANISM: Artificial Sequence
<220> FEATURE:

<223> OTHER INFORMATION: Synthetic DNA

<400> SEQUENCE: 19
aggcaaggat aaaatcgctt agtatggtat tatcgcgcgc                    40

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
tatctgcacg tccacgtaca                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA

<400> SEQUENCE: 21
acttcgtaac cctggtcctt                                          20

<210> SEQ ID NO 22
<211> LENGTH: 40
<212> TYPE: DNA
<213> ORGANISM: Artificial Sequence
<220> FEATURE:
<223> OTHER INFORMATION: Synthetic DNA

<400> SEQUENCE: 22
cgcaaaagaa aatgccgata acgcgcgcct cgcattcgcc                    40

<210> SEQ ID NO 23
<211> LENGTH: 40
<212> TYPE: DNA
<213> ORGANISM: Artificial Sequence
<220> FEATURE:
<223> OTHER INFORMATION: Synthetic DNA

<400> SEQUENCE: 23
cgaattcatt gttacctcgc acgcgcgcct cgcattcgcc                    40

<210> SEQ ID NO 24
<211> LENGTH: 40
<212> TYPE: DNA
<213> ORGANISM: Artificial Sequence
<220> FEATURE:
<223> OTHER INFORMATION: Synthetic DNA

<400> SEQUENCE: 24
gtgctacgcc tgaataagtg gcgaggtaac aatgaattcg                    40

<210> SEQ ID NO 25
<211> LENGTH: 40
<212> TYPE: DNA
<213> ORGANISM: Artificial Sequence
<220> FEATURE:
<223> OTHER INFORMATION: Synthetic DNA

<400> SEQUENCE: 25
acgcgcgcct cgcattcgcc gcgaggtaac aatgaattcg                    40

```
<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
ccattaggcg cagaacctaa                                                        20
```

PROCESS FOR PRODUCTION OF L-AMINO ACID

CROSS-REFERENCE TO RELATED APPLICATIONS

This patent application is the U.S. national phase of International Patent Application No. PCT/JP2011/050208, filed Jan. 7, 2011, which claims the benefit of Japanese Patent Application No. 2010-002704, filed Jan. 8, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 11,217 bytes ASCII (Text) file named "710692SequenceListing.txt," created Jul. 5, 2012.

TECHNICAL FIELD

The present invention relates to a microorganism to be used for the efficient production of an L-amino acid, and an efficient process for producing an L-amino acid, comprising cultivating said microorganism in a medium.

BACKGROUND ART

As a process for producing an L-amino acid, particularly L-glutamine, by a fermentation method, many methods using a coryneform bacterium are known. Examples of such process for producing L-glutamine include a method using a coryneform bacterium imparted with azaserine resistance (patent document 1), a method using coryneform bacterium imparted with 6-diazo-5-oxo-norleucine resistance (patent document 2) and the like.

In addition, as a process for producing L-glutamine using a coryneform bacterium with enhanced glutamine synthetase activity, a method using a coryneform bacterium showing a decreased activity of glutamine synthetase adenylyltransferase which controls a glutamine synthetase via adenylylation (non-patent document 1, patent document 3), a method using a coryneform bacterium wherein the 405th amino acid residue in the ORF of glutamine synthetase that is subject to adenylylation by glutamine synthetase adenylyl transferase is substituted (non-patent document 1, patent document 4) and a, method using a coryneform bacterium in which an activity of PII protein is decreased (non-patent document 2, patent document 3) and the like are known.

As a process for producing L-glutamine by using *Escherichia coli*, only a method using *Escherichia coli* having a glutamine synthetase without an adenylylation ability has been reported (patent document 4).

It has been reported that YeiG encoded by yeiG gene in *Escherichia coli* has a serine esterase motif and has a carboxylesterase activity (non-patent document 3). Also, it has been suggested that it acts in a glutathione-dependent formaldehyde detoxification pathway since it has a high hydrolyzing activity against formylglutathione.

The expression of formylglutathione hydrolase encoded by the frmB (yaiM) gene of *Escherichia coli* is induced by the presence of formaldehyde in the medium (non-patent document 3). However, since YeiG is constitutively expressed even in the absence of formaldehyde in the medium, it may have an unknown function.

A process for producing L-glutamine, which uses a microorganism highly expressing YeiG, is not known, and whether YeiG is involved in the amino acid synthesis and what influence the high expression of YeiG exerts on the amino acid synthesis are not known.

DOCUMENT LIST

Patent Documents patent document 1: JP-A-S55-148094
patent document 2: JP-A-H3-232497
patent document 3: JP-A-2002-300887
patent document 4: JP-A-2003-164297

Non-Patent Documents non-patent document 1: FEMS Microbiol. Lett., 201, 91-98 (2001)
non-patent document 2: FEMS Microbiol. Lett., 173, 303-310(1999)
non-patent document 3: Jour. Biol. Chem., 281, 12514-14522 (2006)

SUMMARY OF THE INVENTION

Problems to be Solved by the Invention

An object of the present invention is to provide an efficient process for producing an L-amino acid by using a microorganism belonging to the genus *Escherichia*.

Means of Solving the Problems

The present invention relates to the following (1)-4).

(1) A process for producing an L-amino acid comprising; culturing a microorganism in which an activity of the protein of any of the following [1]-[3] is increased compared to the parent strain in a medium, producing and accumulating the L-amino acid in the medium, and recovering the L-amino acid from the medium:
[1] a protein comprising the amino acid sequence shown in SEQ ID NO: 2
[2] a protein consisting of an amino acid sequence in which one or more amino acids are deleted, substituted or added in the amino acid sequence shown in SEQ ID NO: 2, and having YeiG activity
[3] a protein consisting of an amino acid sequence having 80% or more homology to the amino acid sequence shown in SEQ ID NO: 2, and having YeiG activity.
(2) The process for producing the L-amino acid of (1), wherein the microorganism is transformed with the DNA of any of the following
[1]-[3], or a microorganism in which an expression of the gene is increased compared to the parent strain by modifying an expression regulatory sequence of the DNA:
[1] a DNA encoding the protein of any of [1]-[3] in (1)
[2] a DNA comprising the nucleotide sequence shown in SEQ ID NO: 1
[3] a DNA which hybridizes to the DNA consisting of a nucleotide sequence complementary to the nucleotide sequence shown in SEQ ID NO: 1 under stringent conditions, and encodes for a protein having YeiG activity.
(3) The process for producing the L-amino acid of (1) or (2), wherein the microorganism belongs to the genus *Escherichia*.

(4) The process for producing the L-amino acid according of any of (1) - (3), wherein the L-amino acid is L-glutamine.

Effect of the Invention

The present invention can provide an efficient process for producing an L-amino acid by using a microorganism.

DESCRIPTION OF EMBODIMENTS

1. Microorganism used for the Process of the Present Invention (1) Microorganism in which YeiG Activity is Increased Compared with that of the Parent Strain In the present specification YeiG activity refers to the activity of a protein consisting of the amino acid sequence shown in SEQ ID NO: 2, and a protein having YeiG activity in the present specification refers to a protein having an activity substantially equivalent to that of a protein consisting of the amino acid sequence shown in SEQ ID NO: 2.

A microorganism in which YeiG activity is increased compared with that of the parent strain is (a) i) a microorganism in which a specific activity of the protein is increased compared with that of the parent strain or ii) a microorganism in which a production amount of YeiG is increased compared with that of the parent strain, which is obtained by modifying a gene encoding YeiG on the chromosomal DNA of the parent strain, or (b) a microorganism obtained by transforming the parent strain with a DNA encoding YeiG. The parent strain in the present specification may be a wild type strain or a mutant strain, and is the original strain before modification or transformation. As the parent strain, for example, wild type strains of E. coli K-12 strain, B strain, B/r strain, and mutant strains thereof can be mentioned, when the microorganism is Escherichia coli. As the mutant strain, E. coli XL1-Blue, E. coli XL2-Blue, E. coli DH1, E. coli MC1000, E. coli ATCC 12435, E. coli W1485, E. coli JM109, E. coli HB101, E. coli No.49, E. coli W3110, E. coli NY49, E. coli MP347, E. coli NM522, E. coli BL21, E. coli ME8415 and the like can be mentioned.

As a protein having YeiG activity, a protein of any of the following [1]-[3] can be mentioned:

[1] a protein comprising the amino acid sequence shown in SEQ ID NO: 2
[2] a protein consisting of an amino acid sequence in which one or more amino acids are deleted, substituted or added in the amino acid sequence shown in SEQ ID NO: 2, and having YeiG activity
[3] a protein consisting of an amino acid sequence having 80% or more homology to the amino acid sequence shown in SEQ ID NO: 2, and having YeiG activity.

In the above, a protein consisting of an amino acid sequence in which one or more amino acids are deleted, substituted or added in the amino acid sequence shown in SEQ ID NO: 2, and having YeiG activity can be obtained, for example, by introducing a site-directed mutation into a DNA encoding a protein consisting of the amino acid sequence shown in SEQ ID NO: 2, by the site-directed mutagenesis method described in Molecular Cloning, A Laboratory Manual, Third Edition, Cold Spring Harbor Laboratory Press (1989) (hereinafter to be abbreviated as Molecular Cloning, 3rd edition), Current Protocols in Molecular Biology, John Wiley & Sons (1987-1997) (hereinafter to be abbreviated as Current Protocols in Molecular Biology), Nucleic Acids Research, 10, 6487 (1982), Proc. Natl. Acad. Sci. USA, 79, 6409(1982), Gene, 34, 315 (1985), Nucleic Acids Research, 13, 4431 (1985), Proc. Natl. Acad. Sci. USA, 82, 488 (1985) and the like.

While the number of amino acid residues to be deleted, substituted or added is not particularly limited, it is around a number that can be deleted, substituted or added by a well-known method such as the above-mentioned site-directed mutagenesis method and the like, and is 1 to several dozen, preferably 1 to 20, more preferably 1 to 10, still more preferably 1 to 5.

The amino acid sequence in which one or more amino acids are deleted, substituted or added in the amino acid sequence shown in SEQ ID NO: 2 means that single or multiple amino acid residues may be deleted, substituted or added at any position(s) in the same sequence.

Examples of the position of the amino acid at which amino acid residues can be deleted or added include 10 amino acid residues on the N-terminal side and the C-terminal side of the amino acid sequence shown in SEQ ID NO: 2.

The deletion, substitution and addition may occur simultaneously, and the amino acid to be substituted or added may be of a natural type or a non-natural type. Examples of the natural type amino acid include L-alanine, L-asparagine, L-aspartic acid, L-arginine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

The following shows examples of mutually substitutable amino acids. The amino acids included in the same group are mutually substitutable.

group A: leucine, isoleucine, norleucine, valine, norvaline, alanine, 2-aminobutanoic acid, methionine, 0-methylserine, t-butylglycine, t-butylalanine, cyclohexylalanine group B: aspartic acid, glutamic acid, isoaspartic acid, isoglutamic acid, 2-aminoadipic acid, 2-aminosuberic acid group C: asparagine, glutamine group D: lysine, arginine, ornithine, 2,4-diaminobutanoic acid, 2,3-diaminopropionic acid group E: proline, 3-hydroxyproline, 4-hydroxyproline group F: serine, threonine, homoserine group G: phenylalanine, tyrosine As the protein having YeiG activity, a protein which consists of an amino acid sequence having 80% or more, preferably 90% or more, more preferably 95% or more, still more preferably 97% or more, particularly preferably 98% or more, most preferably 99% or more homology, to the amino acid sequence shown in SEQ ID NO: 2, and having YeiG activity can be mentioned.

Amino acid sequence and nucleotide sequence homologies can be determined using the algorithm BLAST of Karlin and Altschul [Pro. Natl. Acad. Sci. USA, 90, 5873(1993)] or FASTA [Methods Enzymol., 183, 63 (1990)]. Based on this algorithm BLAST, programs called BLASTN and BLASTX have been developed [J. Mol. Biol., 215, 403(1990)]. When nucleotide sequences are analyzed with BLASTN on the basis of BLAST, parameters are set to, for example, Score=100 and wordlength=12. When amino acid sequences are analyzed with BLASTX on the basis of BLAST, parameters are set to, for example, score=50 and wordlength=3. To afford gapped alignment, Gapped BLAST can be utilized as described in Altschul et al. (1997, Nucleic Acids Res. 25:3389-3402). Alternatively, a repetitive search to detect the positional relationship between molecules (Id.) and the relationship between molecules having a common pattern can be performed using PSI-Blast or PHI-Blast. When BLAST, Gapped BLAST, PSI-Blast and PHI-Blast programs are utilized, the default parameters of each program can be used (see http://www.ncbi.nlm.nih.gov.).

That a protein consisting of an amino acid sequence in which one or more amino acids are deleted, substituted or added in the amino acid sequence shown in SEQ ID NO: 2, and having YeiG activity can be confirmed, for example, by transforming the parent strain with a DNA encoding a protein whose activity is desired to be confirmed, measuring formylglutathione hydrolysing activity of the obtained transformant by the method described in Jour. Biol. Chem. 281, 14514 (2006), and comparing the formylglutathione hydrolysing activity of the parent strain.

As the microorganism of the above-mentioned (a) i) in which a specific activity of a protein having YeiG activity is increased compared with that of the parent strain, a microorganism containing a mutant protein having an improved formylglutathione hydrolysing activity as compared to a protein having YeiG activity of the parent strain, since it contains a protein having an amino acid sequence, in which one or more amino acids, preferably 1-10 amino acids, more preferably 1-5 amino acids, still more preferably 1-3 amino acids, are substituted in an amino acid sequence of the protein of the parent strain, can be mentioned.

As a microorganism of the above-mentioned (a) ii) in which production amount of a protein having YeiG activity is increased compared with that of the parent strain, a microorganism in which production amount of a protein having YeiG activity is increased compared with that of the parent strain, since it has a promoter region wherein one or more nucleotides, preferably 1-10 nucleotides, more preferably 1-5 nucleotides, still more preferably 1-3 nucleotides, of the nucleotide sequence in a transcription regulatory region or a promoter region of a gene encoding the protein present on the chromosomal DNA of the parent strain, are substituted can be mentioned.

As a microorganism of the above-mentioned (b) obtained by transforming the parent strain with a DNA encoding a protein having YeiG activity, a microorganism obtained by transforming the parent strain with
[4] a DNA encoding the protein of any of [1]-[3] above
[5] a DNA comprising the nucleotide sequence of a coding region in the nucleotide sequence shown in SEQ ID NO: 1 or
[6] a DNA which hybridizes to a DNA consisting of a nucleotide sequence complementary to the nucleotide sequence of a coding region in the nucleotide sequence shown in SEQ ID NO: 1 under stringent conditions, and encods for a protein having YeiG activity can be mentioned.

As the microorganism; i) a microorganism containing an exogenous DNA encoding a protein having YeiG activity on chromosomal DNA, and ii) a microorganism extrachromosomally containing an exogenous DNA encoding a protein having YeiG activity can be mentioned. That is, the microorganism i) has one or more of newly-introduced such DNAs on chromosomal DNA when the parent strain does not have a DNA encoding a protein having YeiG activity, and has a DNA encoding two or more of newly-introduced such DNAs on chromosomal DNA when the parent strain has a DNA encoding a protein having YeiG activity. The microorganism ii) has a DNA encoding a protein having YeiG activity on plasmid DNA.

The above-mentioned "hybridize" means that a DNA hybridizes to a DNA comprising a particular nucleotide sequence or a part of the DNA. Therefore, the DNA comprising a particular nucleotide sequence or a part of the DNA can be used as a probe for Northern or Southern blot analysis, and the DNA can be used as an oligonucleotide primer for PCR analysis. As a DNA usable as a probe, a DNA of at least 100 bases, preferably not less than 200 bases, more preferably not less than 500 bases can be mentioned, and as a DNA usable as a primer, a DNA of at least 10 bases, preferably not less than 15 bases, can be mentioned.

A method of hybridization experiment of DNA is well known and, for example, those of ordinary skill in the art can determine the conditions for hybridization according to the DESCRIPTION of this application. The conditions for hybridization can be determined according to the conditions described in Molecular Cloning, 2nd edition, 3rd edition (2001), Methods for General and Molecular Bacteriolgy, ASM Press(1994), Immunology methods manual, Academic press(Molecular), and many other standard texts.

The above-mentioned stringent conditions preferably includes incubating a DNA-immobilized filter and a probe DNA in a solution containing 50% formamide, 5×SSC (750 mmol/l sodium chloride, 75 mmol/l sodium citrate), 50 mmol/l sodium phosphate (pH 7.6), 5×Denhardt's solution, 10% dextran sulfate and 20 µg/l denatured salmon sperm DNA at 42° C. overnight and, for example, washing the filter with 0.2×SSC solution at about 65° C., and lower stringent conditions can also be used. The stringent conditions can be changed by adjusting formamide concentration (lower formamide concentration means low stringency), salt concentration and temperature conditions. Low stringent conditions include incubating in a solution containing 6×SSCE (20× SSCE is 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA at 37° C. overnight and washing the filter with 1×SSC, 0.1% SDS solution at 50° C. A lower stringent conditions include hybridization under the above-mentioned low stringent conditions with a solution at a high salt concentration (for example, 5×SSC), followed by washing.

The above-mentioned various conditions can also be set by adding or changing the blocking reagent used to suppress background of the hybridization experiment. The addition of the above-mentioned blocking reagent may accompany change of hybridization conditions to adopt the conditions.

Examples of the DNA hybridizable under the above-mentioned stringent conditions include a DNA having 90% or more, preferably 95% or more, more preferably 97% or more, still more preferably 98% or more, or particularly preferably 99% or more homology, to a DNA consisting of the nucleotide sequence of a coding region in the nucleotide sequence shown in SEQ ID NO: 1, when calculated using the above-mentioned BLAST, FASTA and the like, based on the above-mentioned parameters and the like.

2. Preparation of Microorganism used in the Present Invention (1) Preparation of Microorganism Showing an Increased YeiG Activity as Compared to the Parent Strain Of the microorganisms in which YeiG activity is increased compared with that of the parent strain, a microorganism in which a specific activity of a protein having YeiG activity is higher than that of the parent strain can be obtained by subjecting a DNA encoding a protein having YeiG activity to an in vitro mutagenesis treatment using a mutating agent, or error-prone PCR and the like to introduce a mutation into the DNA, replacing a DNA encoding a protein having YeiG activity before mutation introduction, which is on the chromosomal DNA of the parent strain, with the mutated DNA, by a known method [Proc. Natl. Acad. Sci. U S A., 2000, 6640 (2000)] to prepare a variant that expresses the mutated DNA, and comparing YeiG activity, namely, formylglutathione hydrolysing activity between the parent strain and the variant by the above-mentioned method.

Moreover, of the microorganisms having a higher activity of a protein having YeiG activity than that of the parent strain, a microorganism in which a production amount of the protein is increased compared with that of the parent strain can be confirmed by a method including subjecting a DNA comprising the nucleotide sequence of a transcription regulatory region or a promoter region of a gene encoding a protein having YeiG activity that the parent strain has, for example, 200 bp, preferably 100 bp, on the upstream side of the initiation codon of the protein, to an in vitro mutagenesis treatment or error-prone PCR and the like to introduce a mutation into the DNA, replacing a transcription regulatory region or a promoter region of a gene encoding a protein having YeiG activity before introducing mutation, which is on the chromosomal DNA of the parent strain, with the mutated DNA by a known method [Proc. Natl. Acad. Sci. U S A., 2000, 6640 (2000)] to prepare a variant having a mutated transcription regulatory region or promoter region, and comparing, by RT-PCR or Northern hybridization and the like, the transcription amounts of the gene encoding a protein having YeiG activity of the parent strain and the variant, or a method including comparison of the production amount of a protein having YeiG activity of the parent strain and the variant by SDS-PAGE and the like.

In addition, a microorganism in which a production amount of a protein having YeiG activity is increased compared with that of the parent strain can also be obtained by replacing a promoter region of a gene encoding the a protein having YeiG activity of the parent strain with a known strong promoter sequence.

As such promoter, promoters derived from *Escherichia coli*, phage and the like, such as trp promoter ($P_{trp}$), lac promoter ($P_{lac}$), $P_L$ promoter, $P_R$ promoter, $P_{SE}$ promoter and the like, SPO1 promoter, SPO2 promoter, penP promoter and the like, functionable in *E. coli*. In addition, artificially created promoters such as promoter having two $P_{trp}$ connected in series, tac promoter, lacT7 promoter, let I promoter and the like can also be recited.

A method of obtaining a DNA encoding a protein having YeiG activity and a preparation method of a microorganism obtained by transforming the parent strain with the DNA are explained in detail in the following.

(a) Preparation of DNA Encoding Protein having YeiG Activity

A DNA encoding a protein having YeiG activity can be obtained, for example, by subjecting the chromosomal DNA library of a microorganism, preferably *E. coli*, to Southern hybridization using a probe DNA that can be designed based on the nucleotide sequence of a DNA encoding the protein having YeiG activity of the above-mentioned 1(1), or PCR using a primer DNA that can be designed based on the nucleotide sequence, and a chromosomal DNA of a microorganism, preferably *E. coli*, as a template [PCR Protocols, Academic Press (1990)].

Alternatively, a sequence having 80% or more, preferably 90% or more, more preferably 95% or more, still more preferably 97% or more, particularly preferably 98% or more, or most preferably 99% or more homology, to the nucleotide sequence of a DNA encoding the protein having YeiG activity of the above-mentioned 1(1), is searched in various gene sequence databases, and a DNA encoding a protein having YeiG activity can also be obtained from a chromosomal DNA, cDNA library etc. of the microorganism having the nucleotide sequence, by the above-mentioned method and based on the nucleotide sequence obtained by the search.

The nucleotide sequence of the DNA can be determined by incorporating the obtained DNA as it is or after digestion with a suitable restriction enzyme and the like into a vector by a conventional method, introducing the obtained recombinant DNA into a host cell, and analyzing the nucleotide sequence by a nucleotide sequence analysis method generally used, for example, a dideoxy method [Proc. Natl. Acad. Sci., USA, 74, 5463 (1977)] or by using a nucleotide sequence analyzer such as 3700 DNA analyzer (manufactured by Applied Biosystems) and the like.

As the above-mentioned vector, pBluescript II KS(+) (manufactured by Stratagene), pDIRECT [Nucleic Acids Res., 18, 6069 (1990)], pCR-Script Amp SK(+) (manufactured by Stratagene), pT7Blue (manufactured by Novagen), pCR II (manufactured by Invitrogen), pCR-TRAP (manufactured by GenHunter) and the like can be mentioned.

As the host cell, microorganisms belonging to the genus *Escherichia* and the like can be mentioned. Examples of the microorganisms belonging to the genus *Escherichia* include *E. coli* XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No.49, *E. coli* W3110, *E. coli* NY49, *E. coli* MP347, *E. coli* NM522, *E. coli* BL21, *E. coli* ME8415 and the like.

As a method for introducing a recombinant DNA, any method can be used as long as it can introduce the DNA into the above-mentioned host cell, and examples thereof include a method using a calcium ion [Proc. Natl. Acad. Sci., USA, 69, 2110 (1972)], a protoplast method (JP-A-S63-248394), an electroporation method [Nucleic Acids Res., 16, 6127 (1988)] and the like.

As a result of the determination of the nucleotide sequence, when the obtained DNA is a partial length, full-length DNA can be obtained by subjecting the chromosomal DNA library to a Southern hybridization method using the partial length DNA as a probe and the like.

Furthermore, the object DNA can also be prepared by chemical synthesis based on the determined nucleotide sequence of the DNA and using a 8905 type DNA synthesizer manufactured by Perceptive Biosystems and the like.

As the DNA obtained as mentioned above, for example, a DNA encoding a protein comprising the amino acid sequence shown in SEQ ID NO: 2, and a DNA comprising the nucleotide sequence shown in SEQ ID NO: 1 can be mentioned.

(b) Preparation of Microorganism Transformed with Plasmid Vector Expressing Protein having YeiG Activity The microorganism can be prepared as follows. Based on a DNA encoding a protein having YeiG activity, which is obtained by the above-mentioned method of (a), a DNA fragment with a suitable length, which contains a region encoding a protein having YeiG activity, is prepared as necessary. By substituting the nucleotide(s) in the nucleotide sequence of the DNA encoding a protein having YeiG activity to provide a codon optimal for the expression in a host cell, a transformant in which a production rate of the protein having YeiG activity is increased can be obtained.

A recombinant DNA is prepared by inserting the DNA fragment into the downstream of the promoter of a suitable expression vector.

By introducing the recombinant DNA into a host cell compatible with the expression vector, a transformant in which an activity of a protein having YeiG activity is increased compared with that of the host cell, i.e., parent strain, can be obtained.

As the host cell, microorganism, preferably prokaryote, more preferably bacterium, more preferably microorganism belonging to the genus *Escherichia*, most preferably *E. coli*, can be used.

As the expression vector, a vector which is autonomously replicable or can be incorporated into a chromosome in the above-mentioned host cell, and contains a promoter at a site permitting transcription of a DNA encoding a protein having YeiG activity, is used.

When prokaryote such as *E. coli* and the like is used as a host cell, a recombinant DNA containing a DNA encoding a protein having YeiG activity is preferably autonomously replicable in the prokaryote as well as a recombinant DNA consisting of promoter, ribosome binding sequence, DNA encoding a protein having YeiG activity, and transcription terminator sequence. It may contain a gene for controlling the promoter.

As the expression vector, pColdI (manufactured by Takara Bio), pCDF-lb, pRSF-lb (all manufactured by Novagen), pMAL-c2x (manufactured by New England Biolabs), pGEX-4T-1 (manufactured by GE Healthcare Bio-Sciences), pTrcHis (manufactured by Invitrogen), pSE280 (manufactured by Invitrogen), pGEMEX-1 (manufactured by Promega), pQE-30 (manufactured by QIAGEN), pET-3 (manufactured by Novagen), pKYP10 (JP-A-S58-110600), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript II SK(+), pBluescript II KS(-) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 manufactured by Takara Bio), pUC118 (manufactured by Takara Bio), pPA1 (JP-A-S63-233798) and the like can be mentioned.

The promoter may be any as long as it can function in a host cell such as *E. coli* and the like. For example, promoters derived from *E. coli*, phage and the like, such as trp promoter ($P_{trp}$), lac promoter ($P_{lac}$), $P_L$ promoter, $P_R$ promoter, $P_{SE}$ promoter and the like, SPO1 promoter, SPO2 promoter, penP promoter and the like. In addition, artificially designed/modified promoters such as promoter having two $P_{trp}$ connected in series, tac promoter, lacT7 promoter, let I promoter and the like can also be used.

A plasmid wherein the distance between Shine-Dalgarno sequence which is a ribosome binding sequence, and an initiation codon is adjusted to a suitable distance (e.g., 6-18 bases) is preferably used.

While a recombinant DNA, wherein a DNA encoding a protein having YeiG activity is bound to an expression vector, does not necessarily require a transcription terminator sequence, a transcription terminator sequence is preferably disposed immediately downstream of a structural gene.

Examples of such recombinant DNA include plasmid pTyeiG.

(c) Preparation of Microorganism having DNA Encoding Protein having YeiG Activity, Introduced into Chromosomal DNA By introducing a DNA encoding a protein having YeiG activity, which is obtained by the method of the above-mentioned (a), into any position of chromosomal DNA, a microorganism showing a higher activity of a protein having YeiG activity than the parent strain can also be obtained.

As a method for introducing the DNA encoding a protein having YeiG activity into any position of chromosomal DNA of a microorganism, a method utilizing a homologous recombination can be mentioned. When *E. coli* is used as a host, or a parent strain, the method described in Proc. Natl. Acad. Sci. U S A., 97, 6640 (2000) can be mentioned.

Specific examples of the microorganism in which YeiG activity is increased compared with that of the parent strain, which is prepared according to the above-mentioned method, include *Escherichia coli* JP/pTyeiG having pTyeiG, which is a plasmid vector expressing a protein having YeiG activity.

3. Process for Producing L-amino Acid of the Present Invention

The microorganism of the present invention can be cultivated in a natural medium or synthetic medium capable of efficiently cultivating the microorganism and containing a carbon source, a nitrogen source, inorganic salts and the like utilizable for the microorganism.

As the carbon source, any can be used as long as the microorganism can utilize, and glucose, fructose, sucrose, xylose, arabinose, molasses containing these, saccharified solution of cellulose biomass, glycerol, hydrocarbonates such as starch, starch hydrolysate and the like, organic acids such as acetic acid, propionic acid and the like, alcohols such as ethanol, propanol and the like, and the like can be used.

As the nitrogen source, ammonia, ammonium salts of inorganic acid or organic acid such as ammonium chloride, ammonium sulfate, ammonium acetate, ammonium phosphate and the like, other nitrogen-containing compounds, as well as peptone, meat extract, yeast extract, corn steep liquor, casein hydrolysate, soybean cake and soybean cake hydrolysate, various fermentation bacteria, and digested materials thereof and the like can be used.

As the inorganic salts, potassium monohydrogen phosphate, potassium dihydrogen phosphate, magnesium phosphate, magnesium sulfate, sodium chloride, ferrous sulfate, manganese sulfate, copper sulfate, calcium carbonate and the like can be used.

Culture is generally performed under aerobic conditions such as shaking culture, deep aeration stirring culture and the like. The culture temperature is preferably 15-40° C., and the culture period is generally 5 hr-7 days. During the culture, pH is maintained at 3.0-9.0. The pH is adjusted with inorganic or organic acid, alkaline solution, urea, calcium carbonate, ammonia and the like.

During the culture, an antibiotic such as ampicillin, tetracycline and the like may be added to the medium as necessary.

For cultivation of a microorganism transformed with an expression vector using an inducible promoter as a promoter, an inducer may be added to the medium as necessary. For example, for cultivation of a microorganism transformed with an expression vector using lac promoter, isopropyl-β-D-thiogalactopyranoside and the like may be added to the medium, and for cultivation of a microorganism transformed with an expression vector using trp promoter, indoleacrylic acid and the like may be added to the medium.

By culturing the microorganism of the present invention, which can be obtained by the above-mentioned method, in a medium to allow producing and accumulating an L-amino acid in the medium, and collecting the L-amino acid from the medium, the L-amino acid can be produced.

The L-amino acid produced and accumulated in a medium can be recovered by a conventional method using activated carbon, ion exchange resin and the like, or extraction with an organic solvent, crystallization, thin layer chromatography, high performance liquid chromatography and the like.

Examples of the invention are shown below, to which, however, the invention of this application is not limited.

Example 1

Construction of yeiG Gene-Expressing Plasmid

A yeiG gene-expressing plasmid was constructed according to the following method.

*Escherichia coli* JM101 strain was inoculated into an LB medium [10 g/l Bacto Tryptone (manufactured by Difco), 5 g/l yeast extract (manufactured by Difco), 5 g/l sodium chloride] and cultured at 30° C. overnight. After culture, a chromosomal DNA of the microorganism was isolated and purified by a method using saturated phenol described in Current Protocols in Molecular Biology.

PCR was performed using synthetic DNAs consisting of the nucleotide sequences shown in SEQ ID NOs: 3 and 4 as primer DNAs for yeiG gene amplification.

A reaction mixture (50 μL) containing chromosomal DNA (0.1 μg) as a template, each primer (0.5 μmol/L), Pyrobest DNA polymerase (2.5 units, manufactured by Takara Bio), 10× buffer for Pyrobest DNA polymerase (5 μL, manufactured by Takara Bio), and each 200 μmol/L dNTPs (dATP, dGTP, dCTP and dTTP) was prepared, and PCR was performed by repeating 30 times a step of 15 seconds at 96° C., 30 seconds at 55° C. and 1 min at 72° C.

Amplification of an about 0.8 kb DNA fragment was confirmed, and the DNA fragment was purified according to a conventional method.

The DNA fragment and an expression vector pTrS30 containing trp promoter [prepared from *Escherichia coli* JM109/pTrS30 (FERN 15 BP-5407)] were respectively digested with Hind III and Sac I, DNA fragments were separated by agarose gel electrophoresis, and a restriction enzyme-digested DNA fragments were recovered respectively using a GENECLEAN II kit (manufactured by BIO 101).

The restriction enzyme-digested fragments of 0.8 kb fragment containing a yeiG gene and a pTrs30, which were obtained above, were ligated using a DNA ligation Kit Ver.2 (manufactured by Takara Bio).

The *Escherichia coli* DH5α strain (manufactured by Takara Bio) was transformed with the obtained ligated DNA, and the transformant was selected using ampicillin resistance as an index.

A plasmid was extracted from the colony of the selected transformant according to a known method, and the structure thereof was analyzed using a restriction enzyme, by which the obtainment of an expression vector pTyeiG wherein a yeiG gene was ligated to the downstream of the trp promoter was confirmed.

Example 2

Preparation of Microorganism having Ability to Produce L-glutamine, L-glutamic acid To prepare *Escherichia coli* having an ability to produce L-glutamine, L-glutamic acid, a strain defective in proB encoding γ-glutamic acid kinase and proA encoding γ-glutamyl phosphate reductase on the L-proline synthetic pathway, a strain defective in glnE encoding glutamine synthetase adenylyl transferase, and a strain defective in gltB, gltD encoding glutamic acid synthase were prepared.

(1) Preparation of proBA Gene-Disrupted *Escherichia coli* JM101

(a) Construction of Marker Gene for Gene Disruption

A cat gene and a sacB gene to be used as marker genes for gene disruption and gene substitution of *Escherichia coli* using homologous recombination were isolated according to the following method.

Using synthetic DNAs consisting of the nucleotide sequences shown in SEQ ID NOs: 5 and 6 as a primer set, and pHSG396 as a template, PCR was performed to give a DNA fragment containing the cat gene. PCR was performed using Pyrobest DNA polymerase (manufactured by Takara Bio) and according to the attached explanation. In addition, using synthetic DNAs consisting of the nucleotide sequences shown in SEQ ID NOs: 7 and 8 as a primer set, and a genome DNA of a wild-type strain of *Bacillus subtilis* 168 strain, which was prepared according to a conventional method, as a template, PCR was performed to give a DNA fragment containing the sacB gene.

The DNA fragment containing the cat gene and the DNA fragment containing the sacB gene were respectively purified, and cleaved with Sal I. After a phenol/chloroform treatment and ethanol precipitation, the both were mixed at an equimolar ratio, and ligated using a DNA ligation Kit Ver.2 (manufactured by Takara Bio). The ligation reaction mixture was purified by a phenol/chloroform treatment and ethanol precipitation. Using the resulting mixture as a template, and synthetic DNAs consisting of the nucleotide sequences shown in SEQ ID NOs: 6 and 8 as a primer set, PCR was performed. The obtained amplified DNA was purified using a Qiaquick PCR purification kit (manufactured by QIAGEN) to give a DNA fragment containing the cat gene and the sacB gene (cat-sacB fragment).

(b) Preparation of proBA Gene-Disrupted Strain

Using synthetic DNAs consisting of the nucleotide sequences shown in SEQ ID NOs: 9 and 10, and synthetic DNAs consisting of the nucleotide sequences shown in SEQ ID NOs: 12 and 14 each as a primer set, and a genome DNA of *Escherichia coli* JM101 strain prepared according to a conventional method as a template, the first PCR was performed to give amplified products.

The amplified products purified using a Qiaquick PCR purification kit (manufactured by QIAGEN) and the cat-sacB fragment were mixed at an equimolar ratio. Using the mixture as a template, the second PCR was performed to give an amplified product, which was purified again using a Qiaquick PCR purification kit (manufactured by QIAGEN). The purified DNA fragment was subjected to agarose electrophoresis, by which amplification of an about 4.6 kb DNA fragment containing a peripheral proBA region inserted with the cat-sacB fragment was confirmed.

Using synthetic DNAs consisting of the nucleotide sequences shown in SEQ ID NOs: 9 and 11, and synthetic DNAs shown in SEQ ID NOs: 13 and 14 as respective primer sets, and a genome DNA of JM101 strain as a template, the first PCR was performed to give amplified products.

The amplified products were purified using a Qiaquick PCR purification kit (manufactured by QIAGEN) and mixed at an equimolar ratio. Using the mixture as a template, the second PCR was performed to give an amplified product, which was purified again using a Qiaquick PCR purification kit (manufactured by QIAGEN). The purified DNA fragment was subjected to agarose electrophoresis, by which amplification of an about 2 kb DNA fragment containing a peripheral proBA region defective in proBA gene was confirmed.

Then, *Escherichia coli* JM101 strain was transformed with pKD46, spread on an LB agar medium containing 100 mg/L ampicillin, and cultured at 30° C. to select *Escherichia coli* JM101 strain possessing pKD46 (hereinafter to be referred to as *Escherichia coli* JM101/pKD46).

The DNA fragment containing a peripheral proBA gene region inserted with the cat-sacB fragment obtained above was introduced into *Escherichia coli* JM101/pKD46, which was obtained by cultivation in the presence of 10 mmol/L L-arabinose and 50 µg/ml ampicillin, by an electric pulse method.

The obtained transformant was spread on an LB agar medium (LB+chloramphenicol+ampicillin) containing 25 µg/ml chloramphenicol and 50 µg/ml ampicillin, and cultured, and a chloramphenicol resistant colony was selected. Since a strain with homologous recombination shows chloramphenicol resistance and sucrose sensitivity, the selected colony was replicated onto an LB agar medium containing 10% sucrose, 25 µg/ml chloramphenicol and 50 µg/ml ampicillin (LB+sucrose+chloramphenicol+ampicillin) and LB+chloramphenicol+ampicillin, and a strain showing chloramphenicol resistance and sucrose sensitivity was selected.

The selected strain was subjected to colony PCR using synthetic DNAs consisting of the nucleotide sequences shown in SEQ ID NOs: 7 and 9 as a primer set, by which insertion of the cat-sacB fragment into the site of the proBA gene was confirmed. The strain having the cat-sacB fragment inserted into the site of the proBA gene was cultured in the same manner as above to prepare a competent cell, and the DNA fragment containing a peripheral proBA region disrupted in proBA gene obtained above was introduced by the electric pulse method.

The obtained transformant was cultured in an LB+sucrose agar medium, and a sucrose resistant colony was selected. Since a strain with homologous recombination does not contain a cat-sacB fragment but shows chloramphenicol sensitivity and sucrose resistance, the selected colony was replicated onto an LB+chloramphenicol agar medium and LB+sucrose agar medium, and a strain showing chloramphenicol sensitivity and sucrose resistance was selected.

A strain showing ampicillin sensitivity, that is, a strain without pKD46, was selected from the selected strains, and the strain was subjected to colony PCR using synthetic DNAs consisting of the nucleotide sequences shown in SEQ ID NOs: 9 and 14 as a primer set, by which proBA gene defect was confirmed.

A proBA gene-defective strain was obtained as mentioned above and named as *Escherichia coli* JP strain.

(2) Preparation of glnE Gene-Defective *Escherichia coli*

Using synthetic DNAs consisting of the nucleotide sequences shown in SEQ ID NOs: 15 and 16, and synthetic DNAs consisting of the nucleotide sequences shown in SEQ ID NOs: 18 and 20 each as a primer set, and a genome DNA of *Escherichia coli* JM101 strain prepared according to a conventional method as a template, the first PCR was performed to give amplified products.

The amplified products purified using a Qiaquick PCR purification kit (manufactured by QIAGEN) and the cat-sacB fragment were mixed at an equimolar ratio. Using the mixture as a template, the second PCR was performed to give an amplified product, which was purified again using a Qiaquick PCR purification kit (manufactured by QIAGEN). The purified DNA fragment was subjected to agarose electrophoresis, by which amplification of an about 4.6 kb DNA fragment containing a peripheral glnE region inserted with the cat-sacB fragment was confirmed.

Using synthetic DNAs consisting of the nucleotide sequences shown in SEQ ID NOs: 15 and 17, and synthetic DNAs shown in SEQ ID NOs: 19 and 20 as respective primer sets, and a genome DNA of JM101 strain as a template, the first PCR was performed to give amplified products.

The amplified products were purified using a Qiaquick PCR purification kit (manufactured by QIAGEN) and mixed at an equimolar ratio. Using the mixture as a template, the second PCR was performed to give an amplified product, which was purified again using a Qiaquick PCR purification kit (manufactured by QIAGEN). The purified DNA fragment was subjected to agarose electrophoresis, by which amplification of an about 2 kb DNA fragment containing a peripheral glnE region disrupted in glnE gene was confirmed.

Then, *Escherichia coli* JP strain was transformed with pKD46, spread on an LB agar medium containing 100 mg/L ampicillin, and cultured at 30° C. to select *Escherichia coli* JP strain possessing pKD46 (hereinafter to be referred to as Escherichia coli JP/pKD46). The DNA fragment containing a peripheral glnE gene region inserted with the cat-sacB fragment obtained above was introduced into *Escherichia coli* JP/pKD46, which was obtained by cultivation in the presence of 10 mmol/L L-arabinose and 50 µg/ml ampicillin, by an electric pulse method.

The obtained transformant was spread on an LB agar medium (LB+chloramphenicol+ampicillin) containing 25 µg/ml chloramphenicol and 50 µg/ml ampicillin, and cultured, and a chloramphenicol resistant colony was selected. Since a strain with homologous recombination shows chloramphenicol resistance and sucrose sensitivity, the selected colony was replicated onto an LB agar medium containing 10% sucrose, 25 µg/ml chloramphenicol and 50 µg/ml ampicillin (LB+sucrose+chloramphenicol+ampicillin) and LB+chloramphenicol+ampicillin, and a strain showing chloramphenicol resistance and sucrose sensitivity was selected.

The selected strain was subjected to colony PCR using synthetic DNAs consisting of the nucleotide sequences shown in SEQ ID NOs: 7 and 15 as a primer set, by which insertion of the cat-sacB fragment into the site of the glnE gene was confirmed. The strain having the cat-sacB fragment inserted into the site of the glnE gene was cultured in the same manner as above to prepare a competent cell, and the DNA fragment containing a peripheral glnE region defective in glnE gene obtained above was introduced by the electric pulse method.

The obtained transformant was cultured in an LB+sucrose agar medium, and a sucrose resistant colony was selected. Since a strain with homologous recombination does not contain a cat-sacB fragment but shows chloramphenicol sensitivity and sucrose resistance, the selected colony was replicated onto an LB+chloramphenicol agar medium and LB+sucrose agar medium, and a strain showing chloramphenicol sensitivity and sucrose resistance was selected.

A strain showing ampicillin sensitivity, that is, a strain without pKD46, was selected from the selected strains, and the strain was subjected to colony PCR using synthetic DNAs consisting of the nucleotide sequences shown in SEQ ID NOs: 15 and 20 as a primer set, by which glnE gene disruption was confirmed.

A glnE gene-defective strain was obtained as mentioned above and named as *Escherichia coli* JPE strain.

(3) Preparation of gltB, gltD Gene-Disrupted *Escherichia coli*

Using synthetic DNAs consisting of the nucleotide sequences shown in SEQ ID NOs: 21 and 22, and synthetic DNAs consisting of the nucleotide sequences shown in SEQ ID NOs: 24 and 26 each as a primer set, and a genome DNA of *Escherichia coli* JM101 strain prepared according to a conventional method as a template, the first PCR was performed to give amplified products.

The amplified products purified using a Qiaquick PCR purification kit (manufactured by QIAGEN) and the cat-sacB fragment were mixed at an equimolar ratio. Using the mixture as a template, the second PCR was performed to give an amplified product, which was purified again using a Qiaquick PCR purification kit (manufactured by QIAGEN). The purified DNA fragment was subjected to agarose electrophoresis, by which amplification of an about 4.6 kb DNA fragment containing a peripheral gltB, gltD region inserted with the cat-sacB fragment was confirmed.

Using synthetic DNAs consisting of the nucleotide sequences shown in SEQ ID NOs: 21 and 23, and synthetic DNAs shown in SEQ ID NOs: 25 and 26 as respective primer sets, and a genome DNA of JM101 strain as a template, the first PCR was performed to give amplified products.

The amplified products were purified using a Qiaquick PCR purification kit (manufactured by QIAGEN) and mixed at an equimolar ratio. Using the mixture as a template, the second PCR was performed to give an amplified product, which was purified again using a Qiaquick PCR purification kit (manufactured by QIAGEN). The purified DNA fragment was subjected to agarose electrophoresis, by which amplification of an about 2 kb DNA fragment containing a peripheral gltB, gltD region disrupted in gltB, gltD gene was confirmed.

Then, the DNA fragment containing a peripheral gltB, gltD gene region inserted with the cat-sacB fragment obtained above was introduced into *Escherichia coli* JP/pKD46, which was obtained by cultivation in the presence of 10 mmol/L L-arabinose and 50 µg/ml ampicillin, by an electric pulse method.

The obtained transformant was coated on an LB agar medium (LB+chloramphenicol+ampicillin) containing 25 µg/ml chloramphenicol and 50 µg/ml ampicillin, and cultured, and a chloramphenicol resistant colony was selected. Since a strain with homologous recombination shows chloramphenicol resistance and sucrose sensitivity, the selected colony was replicated onto an LB agar medium containing 10% sucrose, 25 µg/ml chloramphenicol and 50 µg/ml ampicillin (LB+sucrose+chloramphenicol+ampicillin) and LB+chloramphenicol+ampicillin, and a strain showing chloramphenicol resistance and sucrose sensitivity was selected.

The selected strain was subjected to colony PCR using synthetic DNAs consisting of the nucleotide sequences shown in SEQ ID NOs: 7 and 21 as a primer set, by which insertion of the cat-sacB fragment into the site of the gltB, gltD gene was confirmed. The strain having the cat-sacB fragment inserted into the site of the gltB, gitD gene was cultured in the same manner as above to prepare a competent cell, and the DNA fragment containing a peripheral gltB, gltD region disrupted in gltB, gltD gene obtained above was introduced by the electric pulse method.

The obtained transformant was cultured in an LB+sucrose agar medium, and a sucrose resistant colony was selected. Since a strain with homologous recombination does not contain a cat-sacB fragment but shows chloramphenicol sensitivity and sucrose resistance, the selected colony was replicated onto an LB+chloramphenicol agar medium and LB+sucrose agar medium, and a strain showing chloramphenicol sensitivity and sucrose resistance was selected.

A strain showing ampicillin sensitivity, that is, a strain without pKD46, was selected from the selected strains, and the strain was subjected to colony PCR using synthetic DNAs consisting of the nucleotide sequences shown in SEQ ID NOs: 21 and 26 as a primer set, by which gltB, gltD gene defect was confirmed. A gltB, gltD gene-disrupted strain was obtained as mentioned above and named as *Escherichia coli* JPBD strain.

Example 3

Production of L-glutamine

JP strain, JPE strain and JPBD strain obtained in Example 2 were transformed with pTyeiG and pTrs30 obtained in Example 1. The obtained transformants were respectively named as JP/pTyeiG, JP/pTrs30, JPE/pTyeiG, JPE/pTrs30, JPBD/pTyeiG and JPBD/pTrs30.

Transformants obtained above were inoculated in a 8 ml LB medium containing 50 µg/ml ampicillin in a large test tube, and cultured at 30° C. for 17 hr. The culture medium was inoculated at 1% in a 8 ml medium containing 100 µg/ml ampicillin [16 g/L dipotassium hydrogen phosphate, 14 g/L potassium dihydrogen phosphate, 5 g/L ammonium sulfate, 1 g/L citric acid (anhydrous), 5 g/L casamino acid (manufactured by Difco), 10 g/L glucose, 10 mg/L vitamin B1, 25 mg/L magnesium sulfate heptahydrate, 50 mg/L iron sulfate heptahydrate, 100 mg/L L-proline, adjusted with 10 mol/L sodium hydroxide to pH 7.2, and glucose, vitamin B1, magnesium sulfate heptahydrate and iron sulfate heptahydrate were separately autoclaved and added] in a test tube, and cultured at 30° C. for 24 hr. The culture medium was centrifuged and a culture supernatant was obtained. The accumulated amounts of culture products in the culture supernatant were quantified by high performance liquid chromatography (HPLC). The results are shown in Table 1. In glycerol medium, xylose medium and arabinose medium, they were used as carbon sources instead of glucose. The accumulated amounts of the culture products obtained by using these media are shown in Table 2-Table 4.

TABLE 1

| glucose medium | | |
| --- | --- | --- |
| strain | L-Gln (g/l) | L-Glu (g/l) |
| JP/pTrs30 | 0.00 | 0.21 |
| JP/pTyeiG | 0.13 | 0.04 |
| JPE/pTrs30 | 0.21 | 0.03 |
| JPE/pTyeiG | 0.77 | 0.02 |
| JPBD/pTrs30 | 0.00 | 0.27 |
| JPBD/pTyeiG | 1.21 | 0.00 |

TABLE 2

| glycerol medium | | |
| --- | --- | --- |
| strain | L-Gln (g/l) | L-Glu (g/l) |
| JP/pTrs30 | 0.00 | 0.28 |
| JP/pTyeiG | 0.32 | 0.05 |
| JPE/pTrs30 | 0.34 | 0.01 |
| JPE/pTyeiG | 0.56 | 0.01 |
| JPBD/pTrs30 | 0.00 | 0.26 |
| JPBD/pTyeiG | 0.40 | 0.02 |

TABLE 3

| xylose medium | | |
| --- | --- | --- |
| strain | L-Gln (g/l) | L-Glu (g/l) |
| JP/pTrs30 | 0.00 | 0.22 |
| JP/pTyeiG | 0.62 | 0.04 |
| JPE/pTrs30 | 0.34 | 0.06 |
| JPE/pTyeiG | 0.89 | 0.02 |
| JPBD/pTrs30 | 0.00 | 0.10 |
| JPBD/pTyeiG | 0.80 | 0.00 |

TABLE 4

| | arabinose medium | |
|---|---|---|
| strain | L-Gln (g/l) | L-Glu (g/l) |
| JP/pTrs30 | 0.00 | 0.08 |
| JP/pTyeiG | 0.07 | 0.04 |
| JPE/pTrs30 | 0.10 | 0.04 |
| JPE/pTyeiG | 0.75 | 0.01 |
| JPBD/pTrs30 | 0.00 | 0.06 |
| JPBD/pTyeiG | 0.65 | 0.02 |

As shown in Tables 1-4, the strain obtained by introducing plasmid pTrs30 into *Escherichia coli* JP strain was completely free of L-glutamine accumulation, irrespective of which of glucose, glycerol, xylose and arabinose was used as a starting material, whereas JP/pTyeiG strain showing an enhanced expression of yeiG gene by the introduction of plasmid pTyeiG showed L-glutamine accumulation in any medium. Even when other hosts were used, introduction of pTyeiG resulted in a remarkable increase in the accumulated amount of L-glutamine as compared to the introduction of pTrs30.

Industrial Applicability

According to the present invention, a process for producing an L-amino acid comprising; culturing a microorganism in which YeiG activity is increased compared with that of the parent strain in a medium, producing and accumulating an L-amino acid in the medium, and recovering the L-amino acid from the medium can be provided.

Sequence Listing Free Text

SEQ ID NO:3—explanation of artificial sequence: synthetic DNA
SEQ ID NO:4—explanation of artificial sequence: synthetic DNA
SEQ ID NO:5—explanation of artificial sequence: synthetic DNA
SEQ ID NO:6—explanation of artificial sequence: synthetic DNA
SEQ ID NO:7—explanation of artificial sequence: synthetic DNA
SEQ ID NO:8—explanation of artificial sequence: synthetic DNA
SEQ ID NO:9—explanation of artificial sequence: synthetic DNA
SEQ ID NO:10—explanation of artificial sequence: synthetic DNA
SEQ ID NO:11—explanation of artificial sequence: synthetic DNA
SEQ ID NO:12—explanation of artificial sequence: synthetic DNA
SEQ ID NO:13—explanation of artificial sequence: synthetic DNA
SEQ ID NO:14—explanation of artificial sequence: synthetic DNA
SEQ ID NO:15—explanation of artificial sequence: synthetic DNA
SEQ ID NO:16—explanation of artificial sequence: synthetic DNA
SEQ ID NO:17—explanation of artificial sequence: synthetic DNA
SEQ ID NO:18—explanation of artificial sequence: synthetic DNA
SEQ ID NO:19—explanation of artificial sequence: synthetic DNA
SEQ ID NO:20—explanation of artificial sequence: synthetic DNA
SEQ ID NO:21—explanation of artificial sequence: synthetic DNA
SEQ ID NO:22—explanation of artificial sequence: synthetic DNA
SEQ ID NO:23—explanation of artificial sequence: synthetic DNA
SEQ ID NO:24—explanation of artificial sequence: synthetic DNA
SEQ ID NO:25—explanation of artificial sequence: synthetic DNA
SEQ ID NO:26—explanation of artificial sequence: synthetic DNA

---

The invention claimed is:

1. A process for producing an L-amino acid comprising:
culturing a microorganism in which an activity of a protein is increased compared to the parent strain in a medium, producing and accumulating the L-amino acid in the medium, and
recovering the L-amino acid from the medium,
wherein the protein is
[1] a protein comprising the amino acid sequence shown in SEQ ID NO:2, or
[2] a homologous protein consisting of an amino acid sequence having 95% or more identity to the amino acid sequence shown in SEQ ID NO: 2, and having YeiG activity.

2. The process for producing the L-amino acid according to claim 1, wherein the microorganism is transformed with a DNA, or the microorganism has increased expression of the gene encoding the protein compared to the parent strain by modifying an expression regulatory sequence of the DNA, wherein the DNA is
[1] a DNA encoding the protein,
[2] a DNA comprising the nucleotide sequence shown in SEQ ID NO: 1, or
[3] a DNA which hybridizes to the DNA consisting of a nucleotide sequence complementary to the nucleotide sequence shown in SEQ ID NO: 1 under stringent conditions, and encodes a homologous protein having YeiG activity, wherein the stringent conditions including incubating a DNA-immobilized filter and a probe DNA in a solution containing 50% formamide, 5×SSC (750 mmol/l sodium chloride, 75 mmol/l sodium citrate), 50 mmol/l sodium phosphate (pH 7.6), 5×Denhardt's solution, 10% dextran sulfate and 20 μg/l dentured salmon sperm DNA at 42° C. overnight and washing the filter with 0.2×SSC solution at about 65° C.

3. The process for producing the L-amino acid according to claim 1, wherein the microorganism belongs to the genus *Escherichia*.

4. The process for producing the L-amino acid according to claim 3, wherein the L-amino acid is L-glutamine.

5. The process for producing the L-amino acid according to claim 2, wherein the L-amino acid is L-glutamine.

6. The process for producing the L-amino acid according to claim 2, wherein the microorganism belongs to the genus *Escherichia*.

7. The process for producing the L-amino acid according to claim 6, wherein the L-amino acid is L-glutamine.

8. The process for producing the L-amino acid according to claim 1, wherein the L-amino acid is L-glutamine.

9. The process for producing the L-amino acid according to claim 1, wherein the protein is a protein comprising the amino acid sequence shown in SEQ ID NO: 2.

10. The process for producing the L-amino acid according to claim 1, wherein the protein is a homologous protein consisting of an amino acid sequence having 95% or more identity to the amino acid sequence shown in SEQ ID NO: 2, and having YeiG activity.

11. The process for producing the L-amino acid according to claim 2, wherein the DNA is a DNA encoding the protein.

12. The process for producing the L-amino acid according to claim 2, wherein the DNA is a DNA comprising the nucleotide sequence shown in SEQ ID NO: 1.

13. The process for producing the L-amino acid according to claim 2, wherein the DNA is a DNA which hybridizes to the DNA consisting of a nucleotide sequence complementary to the nucleotide sequence shown in SEQ ID NO: 1 under stringent conditions, and encodes a homologous protein having YeiG activity, wherein the stringent conditions include incubating a DNA-immobilized filter and a probe DNA in a solution containing 50% formamide, 5×SSC (750 mmol/l sodium chloride, 75 mmol/l sodium citrate), 50 mmol/l sodium phosphate (pH 7.6), 5×Denhardt's solution, 10% dextran sulfate and 20 μg/l denatured salmon sperm DNA at 42° C. overnight and washing the filter with 0.2×SSC solution at about 65° C.

* * * * *

UNITED STATES PATENT AND TRADEMARK OFFICE
CERTIFICATE OF CORRECTION

PATENT NO.       : 8,859,241 B2
APPLICATION NO.  : 13/520954
DATED            : October 14, 2014
INVENTOR(S)      : Hayashi et al.

It is certified that error appears in the above-identified patent and that said Letters Patent is hereby corrected as shown below:

In the claims:

Claim 2 at column 29, line 40, "including" should read "include"

Claim 2 at column 29, line 45, "dentured" should read "denatured"

Signed and Sealed this
Ninth Day of June, 2015

Michelle K. Lee
*Director of the United States Patent and Trademark Office*